United States Patent
Takemoto et al.

(10) Patent No.: US 10,500,794 B2
(45) Date of Patent: Dec. 10, 2019

(54) METHOD OF JOINING RESIN TUBES

(71) Applicant: Ushio Denki Kabushiki Kaisha, Tokyo (JP)

(72) Inventors: Fumitoshi Takemoto, Tokyo (JP); Makoto Wasamoto, Tokyo (JP); Shinji Suzuki, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 271 days.

(21) Appl. No.: 15/559,394

(22) PCT Filed: Mar. 3, 2016

(86) PCT No.: PCT/JP2016/056527
§ 371 (c)(1),
(2) Date: Sep. 18, 2017

(87) PCT Pub. No.: WO2016/147874
PCT Pub. Date: Sep. 22, 2016

(65) Prior Publication Data
US 2018/0161554 A1 Jun. 14, 2018

(30) Foreign Application Priority Data
Mar. 19, 2015 (JP) .................................. 2015-055677

(51) Int. Cl.
*B29C 65/00* (2006.01)
*B29C 65/14* (2006.01)
(Continued)

(52) U.S. Cl.
CPC ....... *B29C 66/028* (2013.01); *A61M 25/0015* (2013.01); *A61M 25/1025* (2013.01);
(Continued)

(58) Field of Classification Search
CPC ... B29C 59/085; B29C 59/103; B29C 59/142; B29C 59/165; A61M 25/1025; B29L 2031/7543
See application file for complete search history.

(56) References Cited

U.S. PATENT DOCUMENTS 6,299,596 B1 * 10/2001 Ding ...................... A61L 29/12
604/96.01

FOREIGN PATENT DOCUMENTS

JP  2002-524597 A  8/2002
JP  2007-312942 A  12/2007
(Continued)

OTHER PUBLICATIONS

International Search Report issued in PCT/JP2016/056527; dated May 24, 2016.

*Primary Examiner* — Christopher T Schatz
(74) *Attorney, Agent, or Firm* — Studebaker & Brackett PC (57) ABSTRACT

An object of the present invention is to provide a method of joining resin tubes, in which the degree of freedom of selecting a tube material is large, and further a defect such as stiffness and contraction at joining portions of the tubes is not developed. The method of joining resin tubes according to the present invention is a method of joining resin tubes so that a first tube is joined to a second tube, the first tube and the second tube each being made of synthetic resin, the method comprising: a surface activation step of activating each of a joining region of the first tube and a joining region of the second tube; and an adhesion step of adhering the joining region of the first tube obtained via the surface activation step with the joining region of the second tube obtained via the surface activation step to each other.

8 Claims, 5 Drawing Sheets

(51) Int. Cl.
    *B29C 59/14* (2006.01)
    *B29C 59/16* (2006.01)
    *B29C 59/08* (2006.01)
    *B29C 59/10* (2006.01)
    *A61M 25/00* (2006.01)
    *A61M 25/10* (2013.01)

(52) U.S. Cl.
    CPC .......... *B29C 59/085* (2013.01); *B29C 59/103* (2013.01); *B29C 59/142* (2013.01); *B29C 59/165* (2013.01); *B29C 65/1406* (2013.01); *B29C 65/1496* (2013.01); *B29C 66/11* (2013.01); *B29C 66/52272* (2013.01); *B29C 66/12821* (2013.01); *B29C 66/929* (2013.01)

(56) References Cited

FOREIGN PATENT DOCUMENTS

| | | |
|---|---|---|
| JP | 2012-101359 A | 5/2012 |
| JP | 5201240 B2 | 6/2013 |

\* cited by examiner

METHOD OF JOINING RESIN TUBES

TECHNICAL FIELD

The present invention relates to a method of joining resin tubes so that a first tube is joined to a second tube, the first tube and the second tube each being made of synthetic resin.

BACKGROUND ART

As conventional methods of joining resin tubes to each other, known are a method in which heat sealing is performed and a method in which an adhesive is used.

For example, Patent Document 1 discloses a method of joining resin tubes, the method including connecting two resin tubes to each other at their open ends by heat sealing. Further, Patent Document 2 discloses a method of joining a resin tube for a balloon section with a resin tube for a catheter section in manufacture of a balloon catheter, in which heat sealing is performed, or an ultraviolet curable adhesive is used for joining.

CITATION LIST

Patent Document

Patent Document 1: Japanese Unexamined Patent Application, Publication No. 2012-101359
Patent Document 2: Japanese Patent No. 5201240

SUMMARY OF THE INVENTION

Problems to be Solved by the Invention

However, the conventional methods of manufacturing a resin tube may suffer the following problems.

The method of joining by performing heat sealing can be used only when a resin of one tube and a resin of the other tube are well compatible with each other. Therefore, the method of joining by performing heat sealing is usually difficult to perform when a material of one tube and a material of the other tube are different from each other, resulting in a problem in that the degree of freedom of material selection is small.

Moreover, a surface portion of each of the tubes needs to be subjected to significant thermal fusion even when a resin of one tube and a resin of the other tube are well compatible with each other. This may result in a problem in that the resulting joining portion is hardened, which may, in turn, impair the flexibility of the resulting tube assembly.

Meanwhile, the method of joining in which an adhesive is used suffers from a problem in that curing of the adhesive may harden the resulting joining portion, which may, in turn, impair the flexibility of the resulting tube assembly.

Further, there is a problem in that the resulting tube assembly may be deformed due to possible contraction of an ultraviolet curable adhesive upon curing.

In particular, adhesive force and reliability are required at a very high level in manufacture of a balloon catheter, and thus an adhesive with a high adhesive force is to be selected. However, such an adhesive may suffer from low workability for joining tubes with each other because it generally has highly viscosity.

Accordingly, an object of the present invention is to provide a method of joining resin tubes, in which the degree of freedom of selecting a tube material is large, and in addition, a defect such as stiffness and contraction at a joining portion of the tubes is not developed.

Means for Solving the Problem

The method of joining resin tubes according to the present invention is characterized by a method of joining resin tubes so that a first tube is joined to a second tube, the first tube and the second tube each being made of synthetic resin, the method comprising:

a surface activation step of activating each of a joining region of the first tube and a joining region of the second tube; and an adhesion step of adhering the joining region of the first tube obtained via the surface activation step with the joining region of the second tube obtained via the surface activation step to each other.

In the above method of joining resin tubes, the surface activation step is preferably an ultraviolet irradiation treatment step of irradiating each of the joining regions of the first and second tubes with a light including a vacuum ultraviolet ray.

Further, the surface activation step is preferably a plasma treatment step of exposing each of the joining regions of the first and second tubes to atmospheric-pressure plasma.

The method of joining resin tubes according to the present invention is characterized by a method of joining resin tubes so that a first tube is joined to a second tube, the first tube and the second tube each being made of synthetic resin, the method including:

a surface activation step of irradiating each of the joining regions of the first and second tubes with light to activate each of the joining regions by using a lamp configured to have a double-tube electric-discharge chamber with a electric-discharge space formed between an inner tube and an outer tube, and to emit a light including a vacuum ultraviolet ray inwardly of the inner tube, and by passing each of the first tube and the second tube through the inside of the inner tube of the lamp with each of the joining regions facing toward the inner tube while the lamp is on; and an adhesion step of adhering the joining region of the first tube obtained via the surface activation step with the joining region of the second tube obtained via the surface activation step to each other.

Preferably, in the method of joining resin tubes according the present invention, the first tube has the joining region on an inner peripheral surface thereof, and the second tube has the joining region on an outer peripheral surface thereof, and the surface activation step includes inserting the second tube into the first tube so that the joining regions are overlapped with each other, and then folding back a portion including the joining region at the first tube to expose the joining regions of the first and second tubes before activating the joining regions of the first and second tubes, and then activating the joining regions of the first and second tubes while maintaining the exposure, and the adhesion step is then performed by returning the folded portion at the first tube to the original state.

Preferably, in the method of joining resin tubes according the present invention, the first tube has the joining region on an inner peripheral surface thereof, and the second tube has the joining region on an outer peripheral surface thereof, and the surface activation step is performed on each of the first tube and the second tube, and the second tube is inserted into the first tube so that the joining region of the first tube is faced toward the joining region of the second tube without making contact with each other, and then the joining region of the first tube is adhered with the joining region of the second tube in the adhesion step.

In each of the methods of joining resin tubes as described above, the inner diameter of the first tube is preferably smaller than the outer diameter of the second tube.

Further, in the aforementioned adhesion step, the adhesion between the joining region of the first tube and the joining region of the second tube is preferably maintained for a predetermined period of time.

Further, in the aforementioned adhesion step, a portion including the joining regions adhered with each other at each of the first tube and the second tube is preferably pressurized in the thickness direction.

Further, in the aforementioned adhesion step, a portion including the joining regions adhered with each other at each of the first tube and the second tube is preferably heated while pressurized in the thickness direction.

Advantageous Effect of the Invention

In the method of joining resin tubes according to the present invention, each of the joining regions of the first and second tubes is activated to modify the material(s) of the tubes at each of the joining regions of the first and second tubes. This can allow a good condition of joining to be achieved even when the first tube and the second tube are made of mutually different materials. Therefore, the degree of freedom for selecting a material(s) for the first tube and the second tube is large, and in addition, thermal fusion of the first tube and the second tube or use of an adhesive is not required. This can eliminate development of a defect such as stiffness and contraction at the joining portions of the tubes.

DESCRIPTION OF EMBODIMENTS

Below, embodiments of the method of joining resin tubes according to the present invention will be described.

The method of joining resin tubes according to the present invention is a method of joining resin tubes so that a first tube is joined to a second tube, the first tube and the second tube each being made of synthetic resin. There is no particular limitation for the materials of the first tube and the second tube which can be used in the method of joining resin tubes according to the present invention, as long as they are synthetic resins. Specific examples of synthetic resin for the first tube and the second tube include silicone resin, fluorine-containing silicone resin, and the like.

Further, the first tube and the second tube may each be made of the same material or mutually different materials.

The method of joining resin tubes according to the present invention includes a surface activation step of activating each of the joining regions of the first and second tubes, and an adhesion step of adhering the joining region of the first tube with the joining region of the second tube to each other. Further, a joining step of joining the first tube with the second tube at the joining regions thereof is performed, if desired, while maintaining a state where the first tube and the second tube are adhered with each other in the adhesion step.

There is no particular limitation for specific details in the method of joining resin tubes according to the present invention, as long as the method includes the surface activation step and the adhesion step, but the following methods A, B, and C are preferred. The following methods A, B, and C represent examples which can be applied to a case where the joining region of the first tube is present on the outer peripheral surface of the first tube, and the joining region of the second tube is present on the inner peripheral surface of the second tube.

[Method A]

Figure 1:
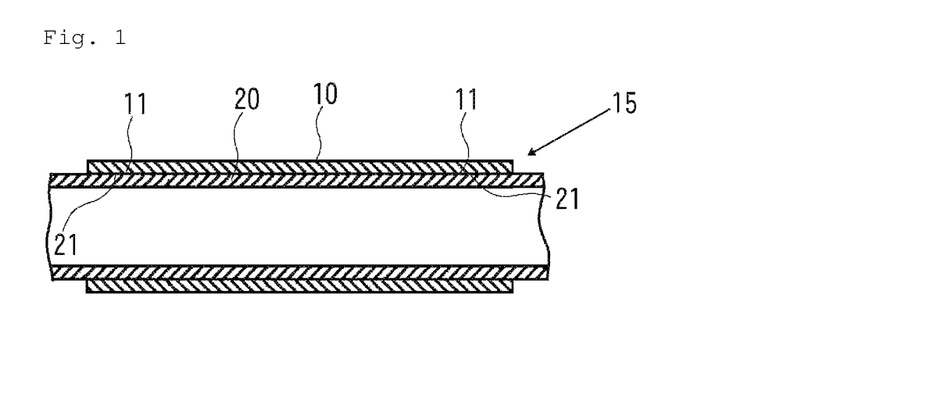
FIG. 1 shows a cross-sectional view illustrating a state where a tube-joining intermediate including a first tube and a second tube is formed in the method A.
Figure 2:
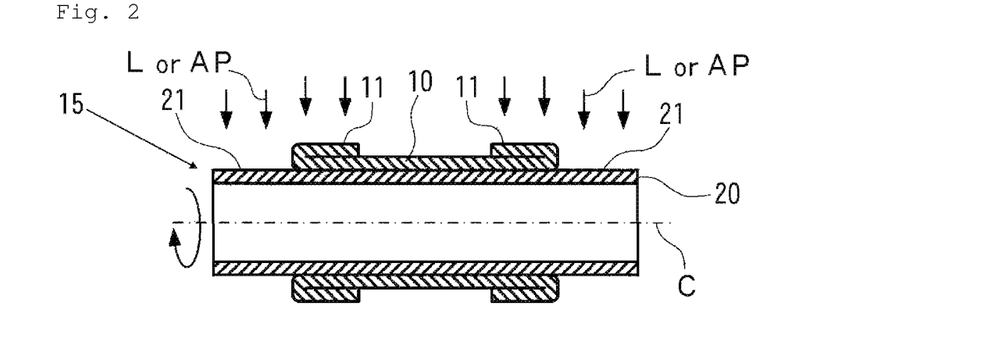
FIG. 2 shows a cross-sectional view illustrating a state where a portion including a joining region of the first tube in the tube-joining intermediate is folded back.

In the surface activation step of the method A, a second tube 20 is inserted into the inside of a first tube 10 so that joining regions 11, 21 of the first tube 10 and the second tube 20 are overlapped with each other to produce a tube-joining intermediate 15 as shown in FIG. 1 before activating the joining regions 11, 21. Then, as shown in FIG. 2, a portion including the joining region 11 at the first tube 10 of the tube-joining intermediate 15 is folded back to expose the joining region 11 of the first tube 10 and the joining region 21 of the second tube 20. Then, the joining regions 11, 21 of the first tube 10 and the second tube 20 are each activated while rotating the tube-joining intermediate 15 around a central axis C of each of the first tube 10 and the second tube 20 as a rotation axis. As described above, each of the joining region 11 of the first tube 10 and the joining region 21 of the second tube 20 can be activated simultaneously in the method A. Arrows in FIG. 2 each represent a light L including a vacuum ultraviolet ray or atmospheric-pressure plasma AP.

<Surface Activation Step>

The surface activation step is preferably either an ultraviolet irradiation treatment step of irradiating each of the joining region 11 of the first tube 10 and the joining region 21 of the second tube 20 with a light including a vacuum ultraviolet ray, or a plasma treatment steps of contacting each of the joining region 11 of the first tube 10 and the joining region 21 of the second tube 20 with atmospheric-pressure plasma.

(1) Ultraviolet Irradiation Treatment Step

Figure 3:
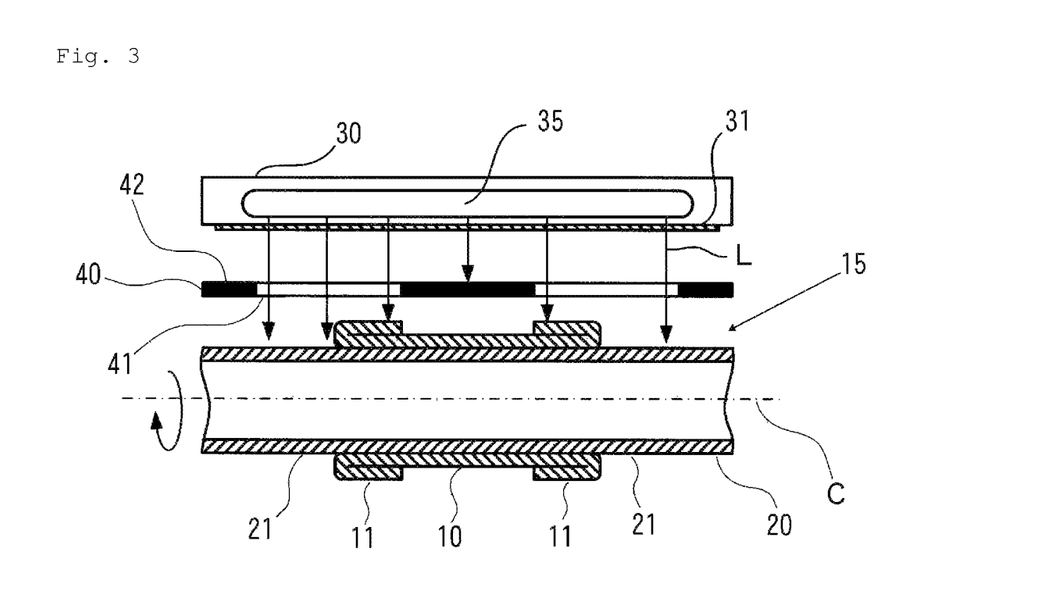
FIG. 3 shows a diagram illustrating the configuration of an exemplary light irradiation device which can be used in an ultraviolet irradiation treatment step.

FIG. 3 shows a diagram illustrating the configuration of an exemplary light irradiation device which can be used in the ultraviolet irradiation treatment step. This light irradiation device has a lamp housing 30 inside which an ultraviolet lamp 35 is positioned. The lamp housing 30 has an ultraviolet-light transmission window 31 through which an ultraviolet light from the ultraviolet lamp 35 is transmitted and emitted to the outside. This ultraviolet-light transmission window 31 is made of, for example, synthetic quartz glass. A mask 40 having a light-transmitting portion 41 and a light-blocking portion 42 is arranged between the ultraviolet-light transmission window 31 and the tube-joining intermediate 15.

As the ultraviolet lamp 35, those which can emit a light L including a vacuum ultraviolet ray, i.e., an ultraviolet light having a wavelength of 200 nm or less may be used.

As the ultraviolet lamp 35 which can emit such a light, the followings can suitably be used: an excimer lamp such as a xenon excimer lamp having an emission line at a wavelength of 172 nm, a low-pressure mercury lamp having an emission line at a wavelength of 185 nm, and a deuterium lamp having an emission line at a wavelength in the range of 120 to 200 nm.

The illuminance level of a vacuum ultraviolet ray emitted to the joining region 11 of the first tube 10 and the joining region 21 of the second tube 20 is, for example, 10 to 20 mW/cm$^2$.

An irradiation time of the light L over the joining region 11 of the first tube 10 and the joining region 21 of the second tube 20 is suitably selected depending on the material(s) of the first tube 10 and the second tube 20, and the illuminance level of a vacuum ultraviolet ray, but it is, for example, between 10 and 120 seconds.

Then, in the ultraviolet irradiation treatment step, the joining regions 11, 21 of the first tube 10 and the second tube 20 are each irritated with the light L from the ultraviolet lamp 35 while rotating the tube-joining intermediate 15 around the central axis C of each of the first tube 10 and the second tube 20 as a rotation axis. This can activate each of the joining regions 11, 21 of the first tube 10 and the second tube 20.

(2) Plasma Treatment Step

Figure 4:
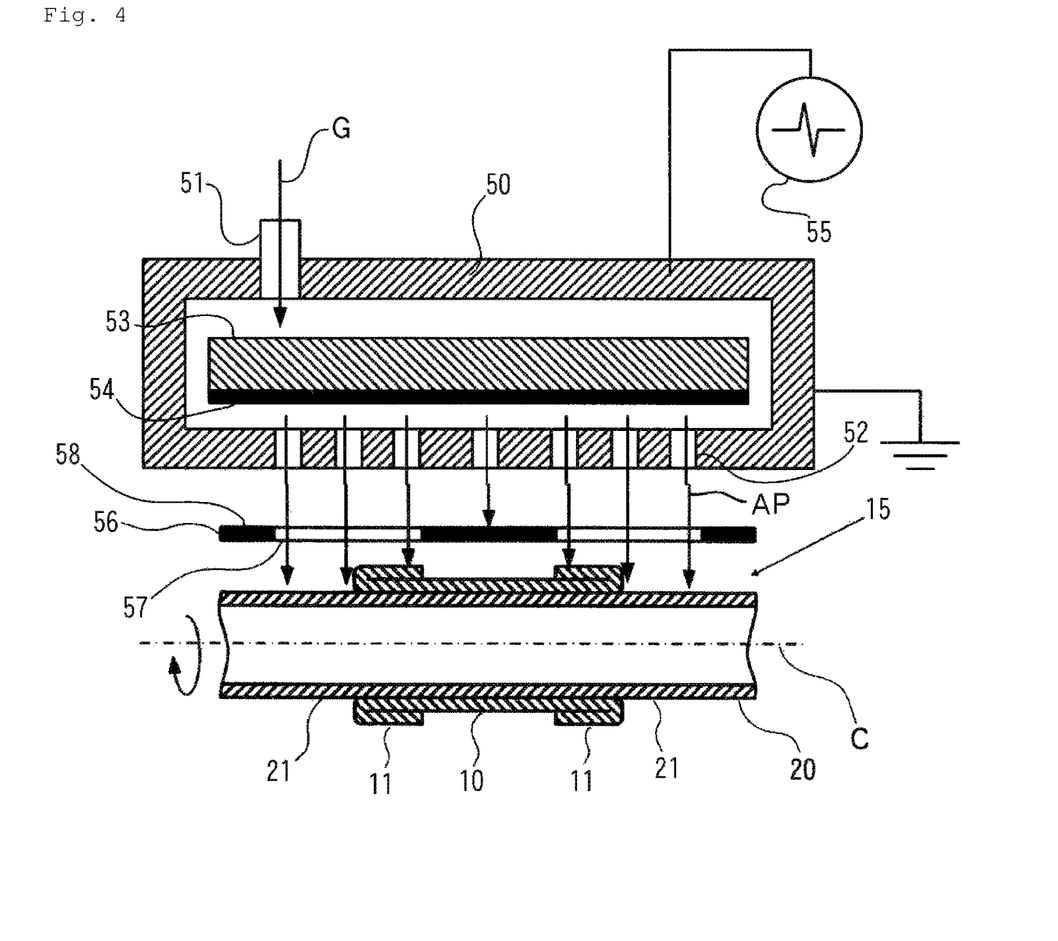
FIG. 4 shows a diagram illustrating the configuration of an exemplary atmospheric-pressure plasma device which can be used in a plasma treatment step.

FIG. 4 shows a diagram illustrating the configuration of an exemplary atmospheric-pressure plasma device which can be used in the plasma treatment step. This atmospheric-pressure plasma device has a housing 50 having a rectangular parallelepiped shape and made of, for example, aluminum. An electrode 53 having a plate-like shape and electrically connected to a high frequency power source 55 is arranged horizontally in the inside of the housing 50. A dielectric layer 54 is formed on the lower surface of the electrode 53. In the exemplary atmospheric-pressure plasma device, the housing 50 is grounded. This means that the electrode 53 serves as a high-voltage side electrode, and the housing 50 serves as an earth-side electrode.

A gas feeding port 51 for feeding a process gas into the housing 50 is provided at the top of the housing 50. Further, a plurality of nozzles 52 for discharging atmospheric-pressure plasma developed inside the housing 50 to the outside are formed at the bottom of the housing 50.

Further, a mask 56 having a passage portion 57 through which atmospheric-pressure plasma discharged from the nozzles 52 is passed and a blockage portion 58 with which atmospheric-pressure plasma is blocked is arranged between the nozzles 52 and the tube-joining intermediate 15.

In the atmospheric-pressure plasma device as described above, a process gas G is fed into the housing 50 through the gas feeding port 51 under the atmospheric pressure or a pressure therearound. When a high frequency electric field is applied between the electrode 53 and the housing 50 through the dielectric layer 54 using the high frequency power source 55 in this configuration, dielectric barrier discharge occurs between the electrode 53 and the housing 50. As a result, the process gas G present between the housing 50 and the dielectric layer 54 is ionized or excited to generate the atmospheric-pressure plasma AP. Then, the atmospheric-pressure plasma AP is discharged to the outside through the nozzles 52 of the housing 50.

In the above configuration, the process gas G preferably includes nitrogen gas, argon gas, or the like as the main component and 0.01 to 5 vol % of oxygen gas. Alternatively, a mixed gas of nitrogen gas and clean dry air (CDA) can also be used.

Further, the electric power supplied from the high frequency power source has a frequency of 20 to 70 kHz and a voltage of 5 to 15 kVp-p.

Moreover, the processing time of plasma treatment is, for example, between 5 and 30 seconds.

Then, in the plasma treatment step, the joining regions 11, 21 of the first tube 10 and the second tube 20 are each contacted with the atmospheric-pressure plasma AP from the atmospheric-pressure plasma device while rotating the tube-joining intermediate 15 around the central axis C of each of the first tube 10 and the second tube 20 as a rotation axis. This can activate each of the joining regions 11, 21 of the first tube 10 and the second tube 20.

<Adhesion Step>

Figure 5:
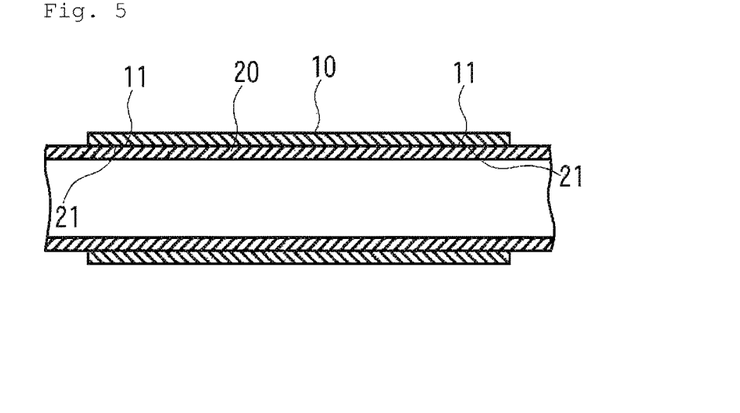
FIG. 5 shows a cross-sectional view illustrating a state where the joining regions of the first and second tubes are adhered with each other in the adhesion step of the method A.

After performing the surface activation step as described above, the folded portion at the first tube 10 is returned to the original state as shown in FIG. 5. Thereby, the adhesion step of adhering the joining region 11 of the first tube 10 with the joining region 21 of the second tube 20 to each other is performed.

In the adhesion step, the adhesion between the joining region 11 of the first tube 10 and the joining region 21 of the second tube 20 is preferably maintained for a predetermined period of time. The holding time of maintaining the adhesion between the joining regions 11 and 21 is preferably 1 to 24 hours, and more preferably 3 to 12 hours.

The adhesion between the joining regions 11 and 21 maintained for a predetermined period of time can ensure reliable joining of the joining region 11 of the first tube 10 to the joining region 21 of the second tube 20.

In the adhesion step where the first tube 10 can be joined to the second tube 20 by adhering the joining region 11 of the first tube 10 with the joining region 21 of the second tube 20, the portion including the joining regions 11, 21 adhered with each other at each of the first tube 10 and the second tube 10 may be pressurized in the thickness direction, or the portion including the joining regions 11, 21 adhered with each other at each of the first tube 10 and the second tube 20 is heated while pressurized in the thickness direction, if desired.

When pressurizing a portion including the joining regions 11, 21, the pressurizing pressure is, for example, 0.1 to 1.0 MPa.

When the first tube 10 has an inner diameter smaller than the outer diameter of the second tube 20, the self-contraction force generated upon returning the folded portion at the first tube to the original state may be used to pressurize the portion including the joining regions 11, 21 of the first tube 10 and the second tube 20. The inner diameter of the first tube differs from the outer diameter of the second tube by, for example, −1.0 to −2.0 mm (a value obtained by subtracting the outer diameter of the second tube from the inner diameter of the first tube).

Further, when heating a portion including the joining regions 11, 21, the heating temperature is, for example, 100 to 200° C.

Moreover, the processing time of pressurization or heat-pressurization is, for example, between 100 and 300 seconds.

[Method B]

Figure 6:
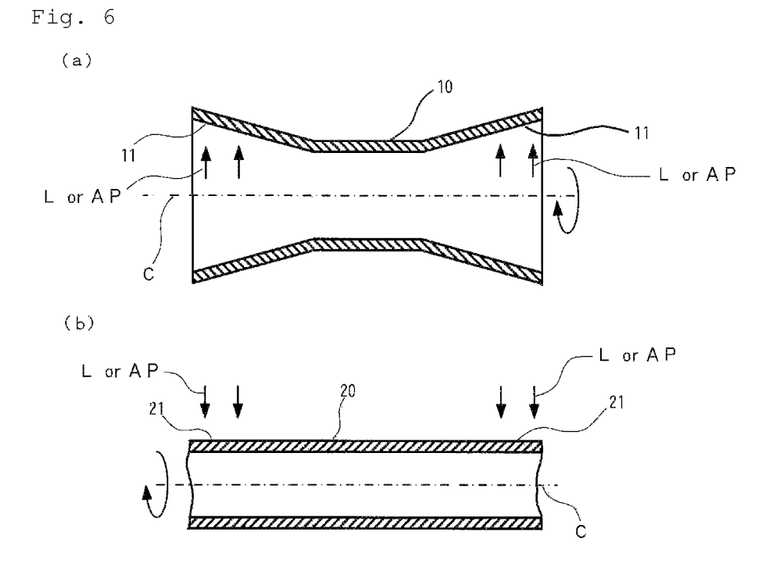
FIG. 6 shows a cross-sectional view illustrating a state where the joining region of the first tube having an increased diameter at a portion including the joining region and the joining region of the second tube are each irritated with light in the ultraviolet irradiation treatment step of the method B.

In the method B, the diameter of a portion including the joining region 11 at the first tube 10 is increased by using an appropriate means, and the joining region 11 is activated while rotating the first tube 10 around the central axis C as a rotation axis as shown in FIG. 6(a). The joining region 21 is also activated while rotating the second tube 20 around the central axis C as a rotation axis as shown in FIG. 6(b). The surface activation step is individually performed on each of the first tube 10 and the second tube 20 as described above.

In the above process, the surface activation step is preferably performed as in the method A, i.e., as in either of the ultraviolet irradiation treatment step of irradiating the light L including a vacuum ultraviolet ray or the plasma treatment step of allowing exposure to an atmospheric-pressure plasma AP.

Specific treatment conditions in the ultraviolet irradiation treatment step and the plasma treatment step are similar to those described for the method A. Further, in the method B, the first tube 10 and the second tube 20 may be subjected to the ultraviolet irradiation treatment step or the plasma treatment step under mutually different conditions.

Figure 7:
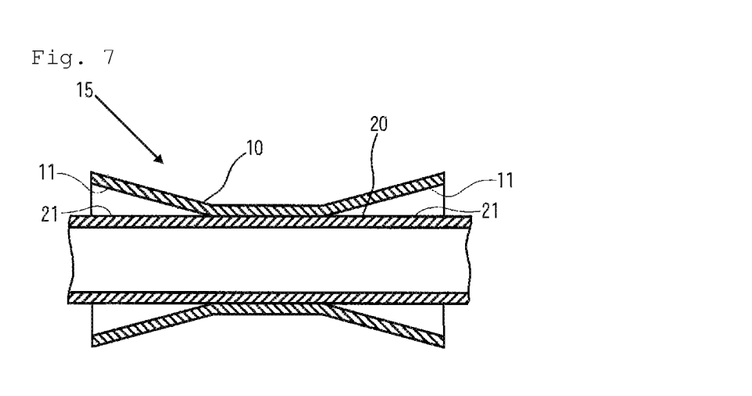
FIG. 7 shows a cross-sectional view illustrating a state where the second tube is inserted into the first tube having an increased diameter at the portion including the joining region in the adhesion step of the method B.
Figure 8:
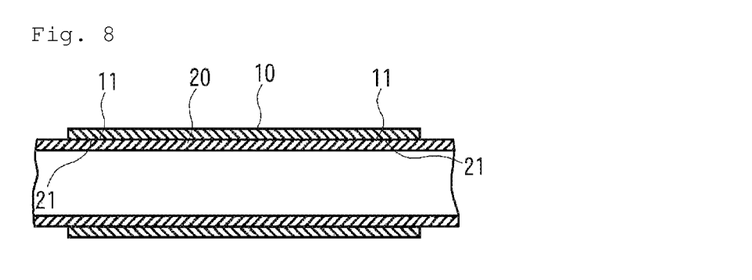
FIG. 8 shows a cross-sectional view illustrating a state where the joining regions of the first and second tubes are adhered with each other in the adhesion step of the method B.

Subsequently, as shown in FIG. 7, the second tube 20 is inserted into the first tube 10 so that the joining region 11 of the first tube 10 is faced toward the joining region 21 of the second tube 20 without making contact with each other while maintaining a state where the diameter of the first tube 10 is increased. Then, as shown in FIG. 8, the joining region 11 of the first tube 10 is allowed to adhere with the joining region 21 of the second tube 20 by releasing the increase in the diameter of the first tube 10. The adhesion step is performed for the joining region 11 of the first tube 10 and the joining region 21 of the second tube 20 as described above.

In the adhesion step of the method B, the adhesion between the joining region 11 of the first tube 10 and the joining region 21 of the second tube 20 is preferably maintained for a predetermined period of time as in the method A.

Further, as in the method A, it is preferred to pressurize the portion including the joining regions 11, 21 adhered with each other at each of the first tube 10 and the second tube 20, or to heat the portion including the joining regions 11, 21 adhered with each other at each of the first tube 10 and the second tube 20 while pressurized in the thickness direction.

Figure 9:
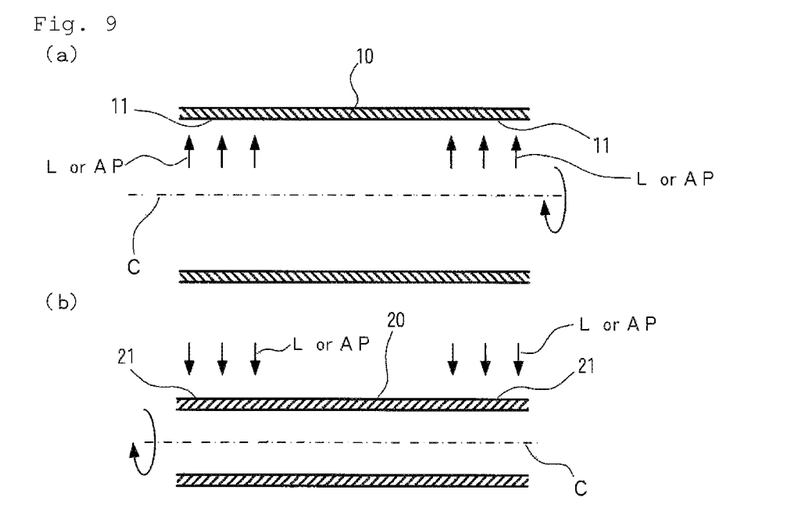
FIG. 9 shows a cross-sectional view illustrating a state where the diameter of the entire first tube and the diameter of the entire second tube are each increased in the surface activation step of the method B.
Figure 10:
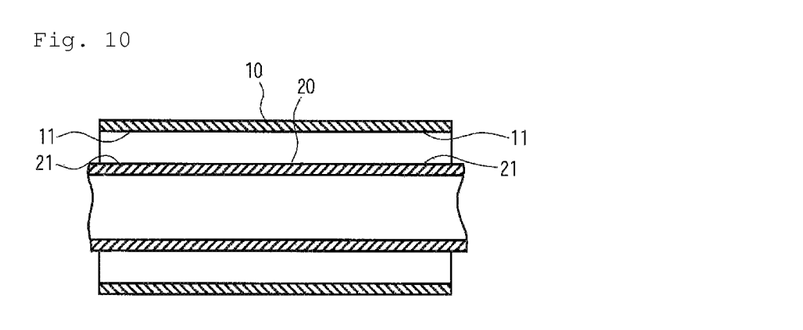
FIG. 10 shows a cross-sectional view illustrating a state where the second tube is inserted into the first tube having an increased diameter throughout the first tube in the adhesion step of the method B.

The diameter of the entire tube 10 may be increased as shown in FIG. 9 when performing the surface activation step in the method B as described above. Further, the second tube 20 may be inserted into the first tube 10 while maintaining a state where the diameter of the entire tube 10 is increased as shown in FIG. 10 when performing the adhesion step.

[Method C]

Figure 11:
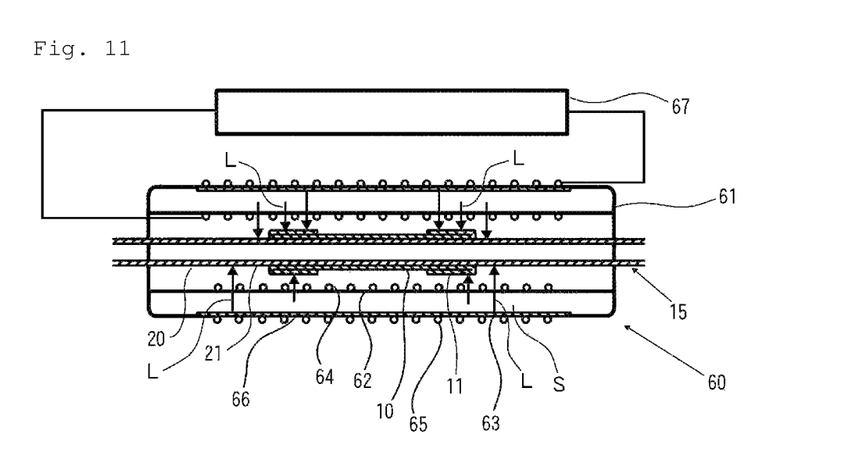
FIG. 11 shows a cross-sectional view cut in the direction of the tube axis illustrating the configuration of an exemplary ultraviolet lamp which can be used in the ultraviolet irradiation treatment step of the method C.
Figure 12:
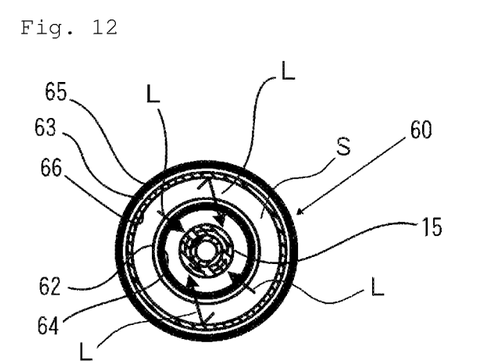
FIG. 12 shows a diagram cut in the direction perpendicular to the tube axis illustrating the configuration of an exemplary ultraviolet lamp which can be used in the ultraviolet irradiation treatment step of the method C.

In the surface activation step of the method C, an ultraviolet lamp 60 configured to have a double-tube electric-discharge chamber 61 with an electric-discharge space S formed between an inner tube 62 and an outer tube 63, and to emit a light including a vacuum ultraviolet ray inwardly of the inner tube 62 as shown in FIGS. 11 and 12.

Specifically, the electric-discharge chamber 61 of the ultraviolet lamp 60 has a linear inner tube 62 made of an dielectric substance and an outer tube 63 made of an dielectric substance, having an inner diameter larger than the outer diameter of the inner tube 62, and arranged so as to surround the inner tube 62 along the tube axis of the inner tube 62. The both ends of the inner tube 62 are air-tightly joined to the both ends of the outer tube 63. This allows a cylindrical electric-discharge space S to be formed between the inner tube 62 and the outer tube 63. The above electric-discharge space S is filled with an electric-discharge gas.

An inner electrode 64 is provided on the inner tube 62 of the electric-discharge chamber 61 so as to make close contact with the inner peripheral surface thereof. Further, an outer electrode 65 is provided on the outer tube 63 of the electric-discharge chamber 61 so as to make close contact with the outer peripheral surface thereof. The inner electrode 64 and the outer electrode 65 are each electrically connected to a high frequency power source 67. Further, an ultraviolet reflection film 66 is formed on the inner peripheral surface of the outer tube 63.

Dielectric substances which can be used for the electric-discharge chamber 61 include those through which a vacuum ultraviolet ray can transmitted, for example, synthetic quartz glass.

The inner electrode 64 is configured to allow a vacuum ultraviolet ray from the electric-discharge space S to pass or be transmitted therethrough. As the inner electrode 64 described above, the followings can be used: for example, those having a structure where an electrically conductive element wire made of aluminum is spirally wound along the inner peripheral surface of the inner tube 62, those having a mesh structure, those having a structure where a film of an electrically conductive material is formed on the inner peripheral surface of the inner tube 62 according to a pattern with gaps such as a mesh, and transparent electrodes through which a vacuum ultraviolet ray can be transmitted.

As the outer electrode 65, those having a configuration similar to that of the inner electrode 64 can be used. They may be non-translucent strip-like electrodes as passage or transmission of a vacuum ultraviolet ray is not necessarily required.

Examples of the ultraviolet reflection film 66 include materials including any of calcium pyrophosphate ($Ca_2P_2O_7$), calcium phosphate ($Ca_3(PO_4)_2$), magnesium pyrophosphate ($Mg_2P_2O_7$), and Ba—Na—Si—O, $SiO_2$, and $Al_2O_3$. Such a material is preferably contained in a percentage of more than 50 mass % relative to the entire ultraviolet reflection film 66.

As the electric-discharge gas, the followings can be used: for example, rare gases such as xenon gas, argon gas, and krypton gas.

In the method C, the first tube 10 is joined to the second tube 20 as follows using the aforementioned ultraviolet lamp 60.

First, a tube-joining intermediate 15 including the first tube 10 and the second tube 20 is produced as in the method A. Then, a portion including the joining region 11 at the first tube 10 is folded back to exposure the joining region 11 of the first tube 10 and the joining region 21 of the second tube 20. Subsequently, the tube-joining intermediate 15 is passed through the inner tube 62 of the ultraviolet lamp 60 while the ultraviolet lamp 60 is on. At this time, each of the joining regions 11, 21 of the first tube 10 and the second tube 20 is faced toward the inner peripheral surface of the inner tube 60. As a result, the joining regions 11, 21 of the first tube 10 and the second tube 20 are each irradiated with the light L from the ultraviolet lamp 60. This can activate each of the joining regions 11, 21 of the first tube 10 and the second tube 20. Subsequently, the adhesion step of adhering the joining region 11 of the first tube 10 with the joining region 21 of the second tube 20 to each other is performed.

According to the above method, the entire surface of each of the joining regions 11, 21 of the first tube 10 and the second tube 20 can be irradiated with the light L without rotating the tube-joining intermediate 15 (the first tube 10 and the second tube 20) in the ultraviolet irradiation treatment step.

According to the method of joining resin tubes as described above, each of the joining region 11 of the first tube 10 and the joining region 21 of the second tube 20 can be activated to modify a material(s) of the tubes at each of the joining regions 11, 21 of the first tube 10 and the second tube 20. Therefore, a good state of joining can be obtained even when the first tube 10 and the second tube 20 are made of mutually different materials. Consequently, the degree of freedom for selecting a material(s) for the first tube 10 and the second tube 20 is large, and in addition, thermal fusion of the first tube 10 and the second tube 20 or use of an adhesive is not required. This can eliminate development of a defect such as stiffness and contraction at the joining portions of the tubes.

The method of joining resin tubes as described above is suitable, for example, as a method for joining a tube for a balloon section to a tube for a catheter section in manufacture of a balloon catheter.

EXAMPLES

Below, specific Examples of the method of joining resin tubes according to the present invention will be described, but the present invention shall not be limited to the following Examples. Further, the following Examples are described in the context of manufacturing a balloon catheter.

[Preliminary Tests for Selecting Conditions]

1. Production of Test Samples

A resin tube for a balloon section made of silicone resin (Shin-Etsu Chemical Co., Ltd.) was cut in the axis direction to prepare a resin sheet. This resin sheet is designated as a "resin sheet a."

A resin tube for a balloon section made of silicone resin (Momentive Performance Materials) was cut in the axis direction to prepare a resin sheet. This resin sheet is designated as a "resin sheet b."

A resin tube for a catheter section made of silicone resin (Wacker Silicones) was cut in the axis direction to prepare a resin sheet. This resin sheet is designated as a "resin sheet c."

2. Selecting Conditions for Surface Activation Step (1) Selecting Conditions for Ultraviolet Irradiation Treatment Step Each of the resin sheets a, b, and c was fixed on a stage in a flattened state, and then irritated with a light from a light irradiation device as shown in FIG. 3 (but without a mask).

In the above experiments, a xenon excimer lamp configured to emit a vacuum ultraviolet light with a central wavelength of 172 nm was used as an ultraviolet lamp, and an ultraviolet-light transmission window made of synthetic quartz glass was used. Conditions for light irradiation are as follows.

Distance from the ultraviolet-light transmission window to a resin sheet: 3 mm

Illuminance at the outer surface of the ultraviolet irradiation window: 40 mW/cm$^2$ Atmosphere around a resin sheet: Air Then, a contact angle with pure water on an irritated surface of a resin sheet was measured with a gradually altered light-irradiation time to determine a light-irradiation time required until the change in the contact angle was stabilized. Results showed that the light-irradiation time for the resin sheet a was 60 seconds, the light-irradiation time for the resin sheet b was 75 seconds, and the light-irradiation time for the resin sheet c was 45 seconds.

(2) Selecting Conditions for Plasma Treatment Step

Each of the resin sheets a, b, and c was fixed on a stage in a flattened state, and exposed to atmospheric-pressure plasma from an atmospheric-pressure plasma device as shown in FIG. 4 (but without a mask).

In the above experiments, the specifications of the atmospheric-pressure plasma device and a process gas used are as follows.

Material of the housing (50): aluminum Material of the electrode (53): super invar (which has a 500-µm alumina film coated on a surface thereof by thermal spray)

Dimensions of the surface of the electrode (53): 50 mm×300 mm

Clearance between the housing (53) and the dielectric layer (54): 0.5 mm

Voltage: 7.0 kVp-p, frequency: 60 kHz, rated power: 1100 VA

Process gas: a mixed gas of nitrogen gas (flow rate: 150 L/min) and clean dry air (flow rate: 1l/min) (the oxygen concentration in the process gas was about 0.14 vol %)

Then, a contact angle with pure water on a surface of a resin sheet exposed to atmospheric-pressure plasma was measured with a gradually altered processing time to determine a processing time required until the change in the contact angle was stabilized. Results showed that the processing time for the resin sheet a was 5 seconds, the processing time for the resin sheet b was 10 seconds, and the processing time for the resin sheet c was 5 seconds.

3. Selecting Conditions for Adhesion Step (Test 1-1)

The resin sheets a and c was irradiated with light under similar conditions as selected for the above ultraviolet irradiation treatment step. The light-irradiation time was 60 seconds for the resin sheet a, and 45 seconds for the resin sheet c.

Subsequently, the resin sheet a was adhered with the resin sheet c so that their light-irradiated surfaces were faced to each other, and pressurized under conditions of a pressurizing pressure of 0.35 MPa and a pressurizing time of 150 seconds using a press machine. Then, the pressure against the resin sheets a and c was released, and the adhesion between the resin sheet a and the resin sheet c was maintained for 24 hours. The state of joining between the resin sheet a and the resin sheet c was evaluated as follows. Results are shown in Table 1.

Method of Evaluating State of Joining:

A joined body including the resin sheet a and the resin sheet c was subjected to a tensile shear test in accordance with JIS K6850. Then, the state of joining was evaluated based on whether peeling occurred between the resin sheets when a tensile shear force of 0.2 MPa was applied to the above joined body for 10 minutes. Specifically, the state of joining was evaluated as good (○) when no peeling occurred between the resin sheets in the above test, and evaluated as poor (x) when peeling occurred between the resin sheets.

(Test 1-2)

The state of joining between the resin sheet a and the resin sheet c was evaluated as in the test 1-1 except that the adhesion between the resin sheet a and the resin sheet c was not maintained after releasing the pressure applied to the resin sheet a and the resin sheet c.

(Test 1-3)

The resin sheets a and c were irradiated with light under similar conditions as in the test 1-1.

Subsequently, the resin sheet a was adhered with the resin sheet c so that their light-irradiated surfaces were faced to each other, and pressurized under conditions of a pressurizing pressure of 0.35 MPa, a pressurizing time of 150 seconds, and a heating temperature of 100° C. using a press machine. Then, the pressure against the resin sheets a and c was released. The state of joining between the resin sheet a and the resin sheet c immediately after releasing pressure was then evaluated as in the test 1-1. Results are shown in Table 1.

(Test 1-4)

The state of joining between the resin sheet a and the resin sheet c immediately after releasing pressure was evaluated as in the test 1-3 except that the light-irradiation time for the resin sheet a was changed to 45 seconds. Results are shown in Table 1.

(Test 1-5)

The state of joining between the resin sheet a and the resin sheet c immediately after releasing pressure was evaluated as in the test 1-4 except that the pressurizing pressure was changed to 0.122 MPa when pressurizing the resin sheets a and c. Results are shown in Table 1.

(Test 1-6)

The resin sheets a and c were positioned so that the distance from the nozzles of the atmospheric-pressure plasma device to a surface to be treated was 3 mm. Then, the atmospheric-pressure plasma device was operated to perform plasma treatment of each of the resin sheets a and c for 5 seconds while feeding nitrogen gas at a flow rate of 150 L/min and clean dry air at a flow rate of 1 L/min as process gases (the oxygen concentration in the process gas was about 0.14 vol %). Subsequently, the resin sheet a was adhered with the resin sheet c so that their treated surfaces were faced to each other, and pressurized under conditions of a pressurizing pressure of 0.35 MPa and a pressurizing time of 150 seconds using a press machine. Then, the pressure against the resin sheets a and c was released. The state of joining between the resin sheet a and the resin sheet c immediately after releasing pressure was then evaluated as in the test 1-1. Results are shown in Table 1.

(Test 2-1)

The state of joining between the resin sheets b and c evaluated as in the test 1-1 except that the resin sheet b was used instead of the resin sheet a, and the light-irradiation time for the resin sheet b was 75 seconds. Results are shown in Table 2.

(Test 2-2)

The resin sheets b and c were irradiated with light under similar conditions as in the test 2-1.

Subsequently, the resin sheet b was adhered with the resin sheet c so that their irradiated surfaces were faced to each other, and pressurized under conditions of a pressurizing pressure of 0.35 MPa, a pressurizing time of 150 seconds, and a heating temperature of 100° C. using a press machine. Then, the pressure against the resin sheets b and c was released. The state of joining between the resin sheet b and the resin sheet c immediately after releasing pressure was then evaluated as in the test 1-1. Results are shown in Table 2.

(Test 2-3)

The state of joining between the resin sheet b and the resin sheet c immediately after releasing pressure was evaluated as in the test 2-2 except that the light-irradiation time for the resin sheet b was changed to 45 seconds. Results are shown in Table 2.

(Test 2-4)

The state of joining between the resin sheet b and the resin sheet c immediately after releasing pressure was evaluated as in the test 2-3 except that the pressurizing pressure was changed to 0.122 MPa when pressurizing the resin sheets b and c. Results are shown in Table 2.

(Test 2-5)

The state of joining between the resin sheet b and the resin sheet c immediately after releasing pressure was evaluated as in the test 2-4 except that the light-irradiation time for each of the resin sheets b and c was changed to 30 seconds. Results are shown in Table 2.

(Test 2-6)

The state of joining between the resin sheet b and the resin sheet c immediately after releasing pressure was evaluated as in the test 2-4 except that the light-irradiation time for each of the resin sheets b and c was changed to 20 seconds. Results are shown in Table 2.

(Test 2-7)

The state of joining between the resin sheet b and the resin sheet c immediately after releasing pressure was evaluated as in the test 2-4 except that the light-irradiation time for each of the resin sheets b and c was changed to 10 seconds. Results are shown in Table 2.

(Test 2-8)

The resin sheets b and c were positioned so that the distance from the nozzles of the atmospheric-pressure plasma device to a surface to be treated was 3 mm. Then, the atmospheric-pressure plasma device was operated to perform plasma treatment for 10 seconds for the resin sheets b and for 5 seconds for the resin sheet c while feeding nitrogen gas at a flow rate of 150 L/min and clean dry air at a flow rate of 1 L/min as process gases (the oxygen concentration in the process gas was about 0.14 vol %). Subsequently, the resin sheet b was adhered with the resin sheet c so that their treated surfaces were faced to each other, and pressurized under conditions of a pressurizing pressure of 0.35 MPa, a pressurizing time of 150 seconds, and a heating temperature of 100° C. using a press machine. Then, the pressure against the resin sheets b and c was released. The state of joining between the resin sheet b and the resin sheet c immediately after releasing pressure was then evaluated as in the test 1-1. Results are shown in Table 2.

TABLE 1

| | Surface activation step | Light-irradiation time or atmospheric-pressure plasma processing time (sec) | | Pressurizing pressure (MPa) | Heating temperature (° C.) | Adhesion-state holding time (h) | State of jointing |
|---|---|---|---|---|---|---|---|
| | | Resin sheet a | Resin sheet c | | | | |
| Test 1-1 | Ultraviolet irradiation treatment step | 60 | 45 | 0.35 | Without heating | 24 | ○ |
| Test 1-2 | Ultraviolet irradiation treatment step | 60 | 45 | 0.35 | Without heating | 0 | ○ |
| Test 1-3 | Ultraviolet irradiation treatment step | 60 | 45 | 0.35 | 100 | 0 | ○ |
| Test 1-4 | Ultraviolet irradiation treatment step | 45 | 45 | 0.35 | 100 | 0 | ○ |
| Test 1-5 | Ultraviolet irradiation treatment step | 45 | 45 | 0.122 | 100 | 0 | ○ |
| Test 1-6 | Plasma treatment step | 5 | 5 | 0.35 | Without heating | 0 | ○ |

TABLE 2

| | Surface activation step | Light-irradiation time or atmospheric-pressure plasma processing time (sec) | | Pressurizing pressure (MPa) | Heating temperature (° C.) | Adhesion-state holding time (h) | State of jointing |
|---|---|---|---|---|---|---|---|
| | | Resin sheet b | Resin sheet c | | | | |
| Test 2-1 | Ultraviolet irradiation treatment step | 75 | 45 | 0.35 | Without heating | 24 | ○ |
| Test 2-2 | Ultraviolet irradiation treatment step | 75 | 45 | 0.35 | 100 | 0 | ○ |
| Test 2-3 | Ultraviolet irradiation treatment step | 45 | 45 | 0.35 | 100 | 0 | ○ |
| Test 2-4 | Ultraviolet irradiation treatment step | 45 | 45 | 0.122 | 100 | 0 | ○ |
| Test 2-5 | Ultraviolet irradiation treatment step | 30 | 30 | 0.122 | 100 | 0 | ○ |
| Test 2-6 | Ultraviolet irradiation treatment step | 20 | 20 | 0.122 | 100 | 0 | ○ |
| Test 2-7 | Ultraviolet irradiation treatment step | 10 | 10 | 0.122 | 100 | 0 | ○ |
| Test 2-8 | Plasma treatment step | 10 | 5 | 0.35 | 100 | 0 | ○ |

As understood from the results from the test 1-2, a good state of joining between the resin sheet a made of silicone resin and the resin sheet c made of silicone resin can be obtained without applying heat when the ultraviolet irradiation treatment step is used as the surface activation step.

Further, as understood from the results from the test 2-1, a good state of joining between the resin sheet b made of silicone resin and the resin sheet c made of silicone resin can be obtained without applying heat when the adhesion is maintained for 24 hours after releasing pressure. The reason of these can be explained as follows.

Even when resins activated by irritation with a vacuum ultraviolet ray are adhered with each other, and light-irritated surfaces of the resins are adhered almost uniformly by applying pressure after adhesion, the joining reaction at an adhesion interface may not occur uniformly throughout the adhesion interface immediately after adhesion. For this reason, when materials relatively less reactive with each other at an adhesion interface are used, a reaction area may be relatively small, and thus the process of joining them may not sufficiently progress. This suggests that a good state of joining may not be obtained due to insufficient adhesion force just after release of pressure. However, the joining reaction at the adhesion interface, which has a prolonged reaction life-time, may be continued and eventually progress throughout the adhesion interface when the surfaces of the resin materials activated by ultraviolet irradiation remain adhered with each other. Therefore, even when the joining reaction is not sufficiently progressed immediately after releasing pressure, maintaining the adhesion for 24 hours may allow the joining reaction to progress throughout the adhesion interface.

In contrast, when materials being relatively more reactive with each other at an adhesion interface are used, reaction areas may be distributed unevenly, but relative large, allowing the reaction for joining the materials with each other to progress sufficiently in a relatively short time.

Further, as understood from the results from the test 2-7, a good state of joining can be obtained immediately after releasing pressure when the light-irradiation time is 10 seconds or more for each of the resin sheets b and c upon joining the resin sheets b and c, and the pressurizing pressure is 0.122 MPa or more, and the heating temperature is 100° C. upon pressurizing the resin sheets b and c.

Moreover, as understood from the results from the test 1-6, a good state of joining can be obtained immediately after releasing pressure when the processing time with atmospheric-pressure plasma is 5 seconds or more for each of the resin sheets a and c upon joining the resin sheet a and c, and the pressurizing pressure is 0.35 MPa or more upon pressurizing the resin sheets a and c in a case where the atmospheric-pressure plasma treatment step is used as the surface activation step.

Moreover, as understood from the results from the test 2-8, a good state of joining can be obtained immediately after releasing pressure when the processing time with atmospheric-pressure plasma is 10 seconds or more for the resin sheet b, and the processing time with atmospheric-pressure plasma is 5 seconds or more for the resin sheet c upon joining the resin sheets b and c, and the pressurizing pressure is 0.35 MPa or more, and the heating temperature is 100° C. upon pressurizing the resin sheets b and c.

Example 1

1. Resin Tube

The following resin tubes were provided as the first tube and the second tube.

The first tube is intended for a balloon section, and made of silicone resin (Momentive Performance Materials), and has an outer diameter of 5.6 mm, an inner diameter of 5.3 mm, an overall length of 40 mm, and a thickness of 0.15 mm.

The second tube is intended for a catheter section, and made of silicone resin (Wacker Silicones), and has an outer diameter of 7.3 mm, an inner diameter of 4.3 mm, and a thickness of 1.5 mm.

Further, the first tube has a joining region extending circumferentially on the inner peripheral surface at the both ends while the second tube has a joining region extending circumferentially on the outer peripheral surface at a location corresponding to the joining region of the first tube. The width in the axis direction of each of the joining regions of the first and section tubes is 10 mm.

2. Ultraviolet Irradiation Treatment Step

The second tube was inserted into the first tube so that their joining regions are overlapped with each other to produce a tube-joining intermediate. Then, a portion including a joining region at the first tube of the tube-joining intermediate was folded back to expose each of the joining regions of the first and second tubes. Then, the ultraviolet irradiation treatment step was performed by irradiating each of the joining regions of the first and second tubes with a light from a light-irradiation device having a configuration as shown in FIG. 3 while rotating the tube-joining intermediate around the central axis of each of the first and second tubes as a rotation axis at a rotation rate of about 0.23 revolutions/second.

In the above step, a xenon excimer lamp configured to emit a vacuum ultraviolet ray with a central wavelength of 172 nm was used as an ultraviolet lamp, and an ultraviolet-light transmission window made of synthetic quartz glass was used. Further, conditions for light irradiation are as follows.

Distance from the ultraviolet-light transmission window to the tube-joining intermediate: 3 mm Illuminance at the outer surface of the ultraviolet irradiation window: 40 mW/cm$^2$ Light-irradiation time: 20 seconds Atmosphere around the tube-joining intermediate: Air 3. Adhesion Step The folded portion of the first tube in the tube-joining intermediate was returned back to the original state to allow the joining region of the first tube and the joining region of the second tube to be adhered with each other. Then the tube-joining intermediate is placed in a thermostatic chamber, and heated under conditions of 100° C. for 150 seconds while pressurizing the portion including the joining regions at a pressurizing pressure of 0.152 MPa with a pressurizing jig to join the first tube to the second tube.

4. Evaluating State of Joining

Air was blown into a gap between the first tube and the second tube of the resulting tube assembly through a preformed air inlet port to inflate the first tube, thereby forming a balloon. After the assembly in this state was allowed to stand for 5 minutes, no air leaking was observed, showing that a good state of joining was achieved.

Further, air bubbles and the like were not present between the joining regions of the first and second tubes when the joining regions of the first and second tubes were observed, showing that they were joined such that the entire joining regions were tightly adhered.

Example 2

The first tube was joined to the second tube as in the Example 1 except that the following resin tubes were used as the first and second tubes, and a portion including the joining regions was not subjected to pressurization with a pressurizing jig in the adhesion step.

The first tube is intended for a balloon section, and made of silicone resin (Momentive Performance Materials), and has an outer diameter of 6.7 mm, an inner diameter of 6.5 mm, an overall length of 40 mm, and a thickness of 0.1 mm.

The second tube is intended for a catheter section, and made of silicone resin (Wacker Silicones), and has an outer diameter of 8 mm, an inner diameter of 5.0 mm, and a thickness of 1.5 mm.

Further, the first tube has a joining region extending circumferentially on the inner peripheral surface at the both ends while the second tube has a joining region extending circumferentially on the outer peripheral surface at a location corresponding to the joining region of the first tube. The width in the axis direction of each of the joining regions of the first and section tubes is 10 mm.

Air was blown into a gap between the first tube and the second tube of the resulting tube assembly through a preformed air inlet port to inflate the first tube, thereby forming a balloon. After the assembly in this state was allowed to stand for 5 minutes, no air leaking was observed, showing that a good state of joining was achieved.

Further, air bubbles and the like were not present between the joining regions of the first and second tubes when the joining regions of the first and second tubes were observed, showing that they were joined such that the entire joining regions were tightly adhered.

Example 3

The first tube was joined with the second tube as in the Example 1 except that the following resin tubes were used as the first and second tubes, and a portion including the joining regions was not subjected to pressurization with a pressurizing jig in the adhesion step.

The first tube is intended for a balloon section, and made of silicone resin (Momentive Performance Materials), and has an outer diameter of 7.3 mm, an inner diameter of 7.0 mm, and a thickness of 0.15 mm.

The second tube is intended for a catheter section, and made of silicone resin (Wacker Silicones), and has an outer diameter of 8 mm, an inner diameter of 5.0 mm, and a thickness of 0.15 mm.

Further, the first tube has a joining region extending circumferentially on the inner peripheral surface at the both ends while the second tube has a joining region extending circumferentially on the outer peripheral surface at a location corresponding to the joining region of the first tube. The width in the axis direction of each of the joining regions of the first and section tubes is 10 mm.

Air was blown into a gap between the first tube and the second tube of the resulting tube assembly through a pre-formed air inlet port to inflate the first tube, thereby forming a balloon. After the assembly in this state was allowed to stand for 5 minutes, no air leaking was observed, showing that a good state of joining was achieved.

Further, a few air bubbles were present between the joining regions of the first and second tubes when the joining regions of the first and second tubes were observed.

EXPLANATION OF REFERENCE NUMERALS

10 First tube
11 Joining region
15 Tube-joining intermediate
20 Second tube
21 Joining region
30 Lamp housing
31 Ultraviolet-light transmission window
35 Ultraviolet lamp
40 Mask
41 Light-transmitting portion
42 Light-blocking portion
50 Housing
51 Gas feeding port
52 Nozzle
53 Electrode
54 Dielectric Layer
55 High frequency power source
56 Mask
57 Passage portion
58 Blockage portion
60 Ultraviolet lamp
61 Electric-discharge chamber
62 Inner tube
63 Outer tube
64 Inner electrode
65 Outer electrode
66 Ultraviolet reflection film
67 High frequency power source
AP Atmospheric-pressure plasma
C Central axis
L Light
S Electric-discharge space

The invention claimed is:

1. A method of joining resin tubes so that a first tube is joined to a second tube, the first tube and the second tube each being made of synthetic resin, the method comprising: a surface activation step comprising of activating each of a joining region of the first tube and a joining region of the second tube; and an adhesion step of adhering the joining region of the first tube obtained via the surface activation step with the joining region of the second tube obtained via the surface activation step to each other, wherein the first tube has the joining region on an inner peripheral surface thereof, and the second tube has the joining region on an outer peripheral surface thereof, and the surface activation step further includes inserting the second tube into the first tube so that the joining regions are overlapped with each other, and then folding back a portion including the joining region of the first tube to expose the joining regions of the first and second tubes before the activating of the joining regions of the first and second tubes, and then performing the activating of the joining regions of the first and second tubes while maintaining the exposure, and the adhesion step is then performed by returning the folded portion of the first tube to the original state.

2. The method of joining resin tubes according to claim 1, wherein the surface activation step is an ultraviolet irradiation treatment step of irradiating each of the joining regions of the first and second tubes with a light including a vacuum ultraviolet ray.

3. The method of joining resin tubes according to claim 1, wherein the surface activation step is a plasma treatment step of exposing each of the joining regions of the first and second tubes to atmospheric-pressure plasma.

4. A method of joining resin tubes so that a first tube is joined to a second tube, the first tube and the second tube each being made of synthetic resin, the method comprising: a surface activation step comprising of irradiating each of joining regions of the first and second tubes with light to activate each of the joining regions by using a lamp configured to have a double-tube electric-discharge chamber with a electric-discharge space formed between an inner tube and an outer tube, and to emit the light including a vacuum ultraviolet ray inwardly of the inner tube, and by passing each of the first tube and the second tube through an inside of the inner tube of the lamp with each of the joining regions facing toward the inner tube while the lamp is on; and an adhesion step of adhering the joining region of the first tube obtained via the surface activation step with the joining region of the second tube obtained via the surface activation step to each other, wherein the first tube has the joining region on an inner peripheral surface thereof, and the second tube has the joining region on an outer peripheral surface thereof, and the surface activation step further includes inserting the second tube into the first tube so that the joining regions are overlapped with each other, and then folding back a portion including the joining region of the first tube to expose the joining regions of the first and second tubes before the irradiating of the joining regions of the first and second tubes, and then performing the irradiating of the joining regions of the first and second tubes while maintaining the exposure, and the adhesion step is then performed by returning the folded portion of the first tube to the original state.

5. The method of joining resin tubes according to claim 1, wherein an inner diameter of the first tube is smaller than the outer diameter of the second tube.

6. The method of joining resin tubes according to claim 1, wherein adhesion between the joining region of the first tube and the joining region of the second tube is maintained for a predetermined period of time in the adhesion step.

7. The method of joining resin tubes according to claim 1, wherein the portion including the joining regions adhered with each other at each of the first tube and the second tube is pressurized in a thickness direction in the adhesion step.

8. The method of joining resin tubes according to claim 1, wherein the portion including the joining regions adhered with each other at each of the first tube and the second tube is heated while pressurized in a thickness direction in the adhesion step.

* * * * *